United States Patent [19]

Ueda et al.

[11] Patent Number: 4,959,207
[45] Date of Patent: Sep. 25, 1990

[54] DEODRANT COMPOSITION, DEODRANT RESIN COMPOSITION AND DEODRANT RESIN SHAPED ARTICLE

[75] Inventors: Tsunehisa Ueda, Zushi; Kouji Miyazaki, Yokohama; Tadao Natsuume, Yokoshuka; Yoshiaki Miki, Yokohama, all of Japan

[73] Assignee: Nippon Zeon Co., Ltd., Tokyo, Japan

[21] Appl. No.: 163,087

[22] Filed: Mar. 2, 1988

[30] Foreign Application Priority Data

| Mar. 2, 1987 | [JP] | Japan | 62-47337 |
| Mar. 2, 1987 | [JP] | Japan | 62-47339 |
| Aug. 7, 1987 | [JP] | Japan | 62-197566 |
| Sep. 10, 1987 | [JP] | Japan | 62-227378 |
| Sep. 11, 1987 | [JP] | Japan | 62-228051 |

[51] Int. Cl.$^5$ ............................................. A61L 2/18
[52] U.S. Cl. ................................. 424/76.1; 422/5; 424/76.5; 424/76.6; 424/76.7
[58] Field of Search ............... 424/76, 76.1, 76.5, 424/76.6, 76.7; 422/5

[56] References Cited

U.S. PATENT DOCUMENTS

| 3,104,205 | 9/1963 | Hainer | 424/76.9 |
| 3,124,460 | 3/1964 | Erwin | 424/76.9 |
| 4,105,610 | 8/1978 | Jung et al. | 525/152 |
| 4,229,410 | 10/1980 | Kosti | 424/76.7 |
| 4,339,550 | 7/1982 | Palinczar et al. | 424/76.3 |
| 4,389,513 | 6/1983 | Miyazaki | 525/381 |
| 4,731,418 | 3/1988 | Dean | 525/205 |

FOREIGN PATENT DOCUMENTS

| 2034565 | 2/1987 | Japan | 424/76.2 |
| 0142559 | 6/1987 | Japan | 424/76.8 |
| 2129183 | 6/1987 | Japan | 424/76.1 |
| 2179464 | 8/1987 | Japan | 424/76.1 |

*Primary Examiner*—Ellis P. Robinson
*Assistant Examiner*—Archene A. Turner
*Attorney, Agent, or Firm*—Sherman and Shalloway

[57] ABSTRACT

A deodorant composition comprising (A) a compound having an acid anhydride group in a molecule and (B) a copper compound, said deodorant composition being useful as a deodorant composite material comprising a substrate (such as a paper, a fabric, a foamed sheet, a pulp, fibers or an inorganic substance) and the deodorant composition included therein, a deodorant resin composition composed of a thermoplastic resin and the deodorant composition, or a shaped article produced by processing the deodorant resin composition.

12 Claims, No Drawings

DEODRANT COMPOSITION, DEODRANT RESIN COMPOSITION AND DEODRANT RESIN SHAPED ARTICLE

This invention relates to a deodorant composition, a deodorant resin composition and a deodorant resin shaped article. More specifically, this invention relates to a deodorant composition excellent in deodorizing activity against malodors of basic and sulfur substances and thermal stability, a deodorant resin composition and a deodorant resin shaped article produced therefrom.

In recent years, with increase in level of living standard, not only malodors occurring in industrial plants but also malodors in daily life (malodors from toilet and sewerage, malodors of garbage and waste matters, malodors given in cooking meat and fish, etc.) have become at issue. These malodors are principally derived from ammonia, amines, hydrogen sulfide and mercaptans. As a method for removing these various malodors in daily life, there are a method wherein fragrant compounds are sprayed or volatilized to mask malodors, a method wherein malodors are adsorbed on activated carbon, and so forth. However, these methods are not said to bring forth satisfactory results.

It has been hitherto known that aliphatic polycarboxylic acids such as citric acid and oxalic acid or their salts are effective as an agent for removing malodors of basic substances such as ammonia and amines (Japanese Laid-Open Patent Publications Nos. 137565/1986 and 154673/1986). Moreover, formation of deodorant resin compositions by blending these compounds with thermoplastic resins has been reported (Japanese Laid-open Patent Application No. 209662/1986). These aliphatic polycarboxylic acids however do not give sufficient deodorizing activity on malodorous substances other than basic substances, and deodorant resin compositions containing these acids have also the same defect; it has been demanded to improve them.

An object of this invention is to solve the above problems.

The present inventors have made extensive studies to achieve the object, and consequently discovered that the conjoint use of (A) a compound having an acid anhydride group in a molecule and (B) a copper compound can provide a deodorant composition excellent in deodorizing activity against malodors of not only basic substances but also sulfur substances (hydrogen sulfide, mercaptans, etc.) and in storage stability, and that the deodorant composition is blended with a thermoplastic resin to give a deodorant resin composition having excellent deodorizing activity.

Thus, the present invention is to provide to a deodorant composition comprising (A) a compound having an acid anhydride group in a molecule and (B) a copper compound, a deodorant resin composition comprising a thermoplastic resin and the deodorant composition, and a deodorant resin shaped article produced therefrom.

The compound (A) having the acid anhydride group in a molecule, used in this invention, may be any compound having a partial structure of formula

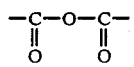

in a molecule. Concrete examples thereof include aromatic polycarboxylic acid anhydrides such as phthalic anhydride, trimellitic anhydride and pyromellitic anhydride; aromatic monocarboxylic acid anhydrides such as benzoic anhydride; chain monocarboxylic acid anhydrides such as butyric anhydride, propionic anhydride and lauric anhydride; chain polycarboxylic acid anhydrides such as succinic anhydride, methylsuccinic anhydride, glutaric anhydride, maleic anhydride, citraconic anhydride, itaconic anhydride and acrylic polymers having an acid anhydride crosslinkage (e.g. polyacrylic anhydride); alicyclic monocarboxylic acid anhydrides such as cyclohexanecarboxylic anhydride and cyclopentanecarboxylic anhydride; alicyclic polycarboxylic acid anhydrides such as 1,2-cyclohexanedicarboxylic anhydride and 3-methyl-$\Delta^4$-tetrahydrophthalic anhydride; and polymers having units derived from alpha,beta-unsaturated dicarboxylic acid anhydrides (hereinafter referred to at times as "alpha,beta-unsaturated dicarboxylic acid anhydride polymers"); and Diels-Alder addition reaction products of alpha,beta-unsaturated dicarboxylic acid anhydrides and olefins and their derivatives.

The acrylic polymers having the acid anhydride crosslinkage used in this invention may be any polymers having an acid anhydride group structure in one and the same molecule or between different molecules of acrylic polymers. Said polymers may be obtained, for example, by subjecting two carboxyl groups to a reaction of dehydration with heating; the method is not particularly limited.

The "acrylic polymers" here referred to are homopolymers of alpha,beta-unsaturated carboxylic acids or copolymers of alpha,beta-unsaturated carboxylic acids and monomers copolymerizable therewith. Concrete examples of the alpha,beta-unsaturated carboxylic acids include acrylic acid, methacrylic acid, crotonic acid, itaconic acid and maleic acid. These are however not critical. The monomers copolymerizable with alpha,beta-unsaturated carboxylic acids are not limited in particular. Concrete examples thereof include (meth)acrylic esters such as methyl methacrylate, ethyl acrylate, butyl methacrylate and 2-ethylhexyl acrylate; aromatic monoolefins such as styrene and alpha-methylstyrene; unsaturated nitriles such as acrylonitrile and methacrylonitrile; vinyl carboxylates such as vinyl acetate and vinyl caproate; aliphatic diolefins such as butadiene and isoprene; and unsaturated acid amides such as acrylamide and N-methylolacrylamide.

A method for obtaining acrylic polymers is not limited in particular. For example, known polymerization methods such as an emulsion polymerization method and a solution polymerization method are available.

The amount of the acid anhydride group contained in the acrylic polymer having the acid anhydride crosslinkage is not particularly limited. It is usually not less than 1 mole %, preferably not less than 5 mole % of all monomer units constituting the acrylic polymer. When the amount is too small, the amount of the deodorant composition relative to the thermoplastic resin becomes too large, posing a problem with shapability of the deodorant resin composition.

The molecular weight of the acrylic polymer is not limited in particular. It is usually 500 to 500,000, preferably 1,000 to 300,000.

When the alpha,beta-unsaturated dicarboxylic acid anhydride polymers are used as the compound having the acid anhydride group in the molecule in this invention, a deodorant composition having excellent thermal stability can result.

The alpha,beta-unsaturated dicarboxylic acid anhydride polymer used in this invention is a homopolymer of an alpha,beta-unsaturated dicarboxylic acid anhydride or a copolymer of the alpha,beta-unsaturated dicarboxylic acid anhydride and one or more kinds of a monomer copolymerizable therewith. A substance of a chemical structure obtained by converting at least part of the acid anhydride group of the alpha,beta-unsaturated dicarboxylic acid anhydride units contained in the homopolymer or copolymer into a carboxyl group via known reaction such as hydrolysis or alcoholysis is also included in the alpha,beta-unsaturated dicarboxylic acid anhydride polymer of this invention.

Concrete examples of the alpha,beta-unsaturated dicarboxylic acid anhydride include maleic anhydride, itaconic anhydride and citraconic anhydride. Of these, maleic anhydride is preferable in reactivity and economy.

Concrete examples of the monomer copolymerizable with the alpha,beta-unsaturated dicarboxylic acid anhydride include aromatic monoolefins such as styrene, alpha-methylstyrene and vinyltoluene; aliphatic monoolefins such as ethylene, propylene, isobutene, 1-butene, 2-butene, 1-pentene, 2-pentene, 2-methyl-1-butene, 2-methyl-2-butene, 1-hexene, 2,2,4-trimethyl-1-pentene, 2,2,4-trimethyl-2-pentene, 1-decene and 1-octadecene; cyclic monoolefins such as cyclopentene, cyclohexene and cyclooctene; aliphatic diolefins such as butadiene, isoprene and piperylene; unsaturated carboxylic acids such as acrylic acid and methacrylic acid; unsaturated carboxylic acid esters such as ethyl acrylate and methyl methacrylate; unsaturated nitriles such as acrylonitrile and methacrylonitrile; vinyl halides such as vinyl chloride; vinyl carboxylates such as vinyl acetate; vinyl ethers such as methyl vinyl ether; and unsaturated sulfonic acids such as vinylsulfonic acid and p-styrenesulfonic acid.

A method for preparing the alpha,beta-unsaturated dicarboxylic acid anhydride polymer is not limited in particular. For example, known polymerization methods such as an emulsion polymerization method and a solution polymerization method are available.

The amount of the units derived from the alpha,beta-unsaturated dicarboxylic acid anhydride is not particularly limited. It is usually not less than 1 mole %, preferably not less than 5 mole % of all monomer units constituting the alpha,beta-unsaturated dicarboxylic acid anhydride polymer. Where the amount is too small, the amount of the deodorant composition relative to the thermoplastic resin goes too large, posing a problem with shapability of the deodorant resin composition.

The molecular weight of the alpha,beta-unsaturated dicarboxylic acid anhydride polymer is not limited in particular. It is usually 500 to 500,000, preferably 1,000 to 300,000.

Examples of the Diels-Alder addition reaction products of alpha,beta-unsaturated dicarboxylic acid anhydrides with olefins are Diels-Alder reaction products of alpha,beta-unsaturated dicarboxylic acid anhydrides with diolefins and ene reaction products of alpha,beta-unsaturated dicarboxylic acid anhydrides with olefins (as to the ene reaction, see H. M. R. Hoffmann, Angew Chem. Int. Ed. 8, 556 (1969). However, these are not critical.

Concrete examples of the alpha,beta-unsaturated dicarboxylic acid anhydrides used in the Diels-Alder addition reaction are maleic anhydride, itaconic anhydride and citraconic anhydride. Of these, maleic anhydride is preferable in reactivity and economy.

The diolefins that allow the Diels-Alder reaction are not particularly limited. Concrete examples thereof are chain conjugated diolefins such as butadiene, isoprene and piperylene; aliphatic trienes such as 1,3,5-hexatriene; cyclic conjugated poly-unsaturated olefins such as cyclopentadiene, 1,3-cyclohexadiene and cyclooctatetraene; and aromatic compounds such as styrene, indene and naphthalene. Other diolefins are compounds described in M. C. Kloetzel et al., "Organic Reactions" vol. 4, pp. 1–60 (John Wiley & Sons, Inc.).

The olefins that allow the ene reaction are not particularly limited. Examples thereof are chain monoolefins such as propylene, isobutene, 1-butene, 2-butene, 1-pentene, 2-pentene, 2-methyl-1-butene, 2-methyl-2-butene, 1-hexene, 2,2,4-trimethyl-1-pentene, 2,2,4-trimethyl-2-pentene, 1-decene, 1-octadecene, and various alpha-olefins obtained by polymerizing lower monoolefins (e.g. ethylene and propylene) in the presence of Ziegler catalysts; cyclic monoolefins such as cyclopentene, cyclohexene and cyclooctene; cyclic non-conjugated diolefins such as 1,4-pentadiene and 1,4-cyclohexadiene; higher unsaturated aliphatic acids such as oleic acid; and polymers having an unsaturated bond, such as polybutadiene.

The derivatives of the Diels-Alder addition reaction products of alpha,beta-unsaturated dicarboxylic acid anhydrides with olefins used in this invention are not limited in particular and may be any substances having a structure derived from Diels-Alder addition reaction products of alpha,beta-unsaturated dicarboxylic acid anhydrides with olefins by a known reaction (including a polymerization reaction). Concrete examples are hydrogenated products of Diels-Alder addition reaction products of alpha,beta-unsaturated dicarboxylic acid anhydrides with olefins; compounds obtained by converting an acid anhydride group of the above addition reaction products into a carboxyl group; compounds obtained by converting an acid anhydride group of the above addition reaction products into a carboxyl group and then conducting the Diels-Alder addition reaction with the above olefins; and compounds obtained by hydrogenating the above compounds.

The deodorant composition of this invention can contain not only one kind but also two or more kinds of the compound having the acid anhydride group in the molecule.

The copper compound (B) in this invention may be an inorganic acid salt, an organic acid salt, a hydroxide, a sulfide, a complex or an oxide of copper. Concrete examples thereof include copper sulfate, copper nitrate, cuprous chloride, cupric chloride, cuprous bromide, cupric bromide, cuprous iodide, copper carbonate, cupric hydroxide, cupric sulfide, copper cyanide, copper acetate, cupric citrate, copper gluconate, copper malate, copper glyoxylate, copper 2-ketoglutarate, copper pyruvate, copper oxaloacetate, copper acid phosphate, copper pyrophosphate, copper chlorophyll, sodium copper chlorophyllin, potassium copper chlorophyllin, copper phthalocyanine, copper porphyrin, copper ethylenediaminetetraacetate, copper acetylacetonate, cuprous oxide, cupric oxide, copper oleate and copper naphthenate. Or a compound containing copper in a high molecular chain in the form of e.g. a copper carboxylate is also available. Of these copper compounds, the inorganic acid salts are preferable in view of cost and availability, and the complexes are preferable in view of safety. The deodorant composition of this invention can contain not only one kind but also two or more kinds of the copper compound.

The ratio of component(A) to component (B) in the deodorant composition of this invention can properly be selected according to the function required of the final product. Component (B) is usually 0.01 to 200 parts by weight, preferably 0.02 to 50 parts by weight, more preferably 0.05 to 20 parts by weight per 100 parts by weight of component (A). When the amount of component (B) is too small, a deodorizing activity on sulfur substances might be poor. On the other hand, when the amount is too large, it might be unwanted in toxicity.

The deodorant composition of this invention may contain, if required, known deodorants, germicides and fungicides, and further additives such as pigments, coloring agents, stabilizers and antioxidants.

A method for preparing the deodorant composition in this invention is not limited in particular. Examples thereof are a method wherein components are formed into a solution with a solvent able to uniformly dissolve them, a method wherein the solution is dried by vacuum drying or spray drying to form a solid matter and a method wherein the components are uniformly mixed by mixing and grinding, etc.

The deodorant composition of this invention can be used either singly in a form of e.g. a solution, a powder or a tablet or as a deodorant resin composition obtained by blending it with a thermoplastic resin as will be later described. Moreover, the deodorant composition of this invention can be used in the form impregnated in or coated on an impregnable or coatable substrate such as a paper, a fabric, a foamed sheet, a pulp or fibers, or in the form supported on an inorganic substrate, i.e. in the form of a deodorant composite material. The inorganic substrate may be any inorganic substrate able to support said composition, concrete examples being activated carbon, alumina, silica gel, zeolite, clay, bentonite, diatomaceous earth and acid clay. The shape of the inorganic substrate is not limited in particular, and may be a powder, granules or fibers.

In this invention, the amount of the deodorant composition to be impregnated in or supported on the above substrate varies with purposes. It is usually 0.1 to 30% by weight, preferably 1.0 to 20% by weight. Where the amount is too small, the deodorizing effect might be insufficient. Meanwhile, where the amount is too large, it might be unwanted in economy.

The deodorant resin composition in this invention which is prepared by blending the aforesaid deodorant composition with the thermoplastic resin is profitable as a starting material of a deodorant resin shaped article.

The thermoplastic resin used in this invention may be any thermoplastic resin if it can be shaped into a film, a sheet, fibers, a foam and other various plastic shaped articles. Concrete examples of the thermoplastic resin include polyolefins such as polyethylene, polypropylene and polybutadiene; polyvinyl compounds such as polyvinyl alcohol, polyvinyl chloride, polyvinylidene chloride, polystyrene, an acrylonitrile/butadiene/styrene copolymer and a vinyl chloride/vinyl acetate copolymer; cellulose esters such as cellulose diacetate; regenerated celluloses; polyesters; polyamides; and fluorocarbon resins.

Examples of an expandable thermoplastic resin to be later described include polyvinyl chloride, a vinyl acetate/vinyl chloride copolymer, polyethylene, polypropylene, polystyrene, an acrylonitrile/butadiene/styrene resin, polyvinyl alcohol, polyamides and celluloses.

The amount of the deodorant composition comprising (A) the compound having the acid anhydride group in the molecule and (B) the copper compound relative to the thermoplastic resin varies with purposes. It is usually 0.1 to 30% by weight, preferably 1.0 to 20% by weight based on the resin. When the amount is too small, the deodorizing activity might be insufficient.

A blending method of the thermoplastic resin and the deodorant composition comprising (A) the compound having the acid anhydride group in the molecule and (B) the copper compound are not particularly limited. Possible examples thereof are a method wherein components (A) and (B) are blended in advance and then blended with the thermoplastic resin, a method wherein part of component (A) and/or part of component (B) is blended with the thermplastic resin, followed by adding the remainder of the deodorant composition, and a method wherein part of the thermoplastic resin is blended with component (A) the remainder of the thermoplastic resin is blended with component (B) and both the blends are mixed to form a deodorant composition of this invention. Further, the deodorant composition of this invention supported on the inorganic substrate such as activated carbon, etc. is suited for blending because of good dispersibility in the thermoplastic resin.

The deodorant resin composition in this invention can contain known deodorants, germicides and fungicides, and further stabilizers, lubricants, antioxidants, ultraviolet absorbers, processing aids, forming agents, pigments, fire retardants and impact-resistant aids unless impairing the function of the deodorant resin composition.

The thus obtained deodorant resin composition in this invention is processed into varied shaped articles including a film, a sheet, etc. by a usual method such as extrusion molding, compression molding, calendering, blow molding or injection molding. Moreover, the deodorant resin composition in this invention can be formed into fibers either singly or in combination with other fibrous starting material. Fine perforations may be formed in the resulting film or sheet by a needle punch to render it air-permeable. Alternatively, a woven fabric, a nonwoven fabric or a paper may be covered by the above film or sheet, or the film or sheet be laminated on another resin film. Fibers may be woven into a fabric or a net.

Where the expandable thermoplastic resin is used, it is also possible that the deodorant resin composition is expansion molded to give a foam. Preparation of the foam from the deodorant resin composition in this invention brings forth an advantage that malodors of ammonia and amines occurring in the expansion of the resin can be extremely reduced.

Thus, the present invention can provide the deodorant composition excellent in deodorizing activity and thermal stability compared to the prior art. This composition is used either singly or in the form impregnated in, coated on, or supported on various substrates as a deodorant, a germicide or a fungicide.

The deodorant resin composition excellent in deodorizing activity and storage stability compared to the prior art can be afforded by blending the deodorant composition of this invention with the thermoplastic resin. The deodorant resin composition is useful as a starting material of a film, a sheet, fibers, a foam and other various plastic shaped articles requiring a deodorizing activity. The various shaped articles produced therefrom are available as materials of products such as clothing, bedding, furniture, wallpaper, food tray, packaging material, filter, etc.

The Following Examples, Comparative Examples and Referential Examples illustrate this invention in more detail. All parts and percentages in these examples are on the weight basis unless otherwise indicated. Moreover, deodorizing tests in these examples were performed as described below unless otherwise indicated.

[Ammonia or methyl mercaptan deodorizing test]

A 150-milliliter glass ampoule with a crown cap was charged with 1 g of each of the samples and stopped. The inside of the ampoule was replaced with a given concentration of ammonia or methyl mercaptan. After a given period of time, the amount of ammonia or methyl mercaptan in the ampoule was measured by gas chromatography.

[Hydrogen sulfide deodorizing test]

A 3-liter odor bag with a silicone rubber stopper was charged with 1 g of each of the samples. One liter of air containing 100 ppm of hydrogen sulfide was then charged therein. After a given period of time, the amount of hydrogen sulfide in the ampoule was measured by a Kitagawa-type gas detector.

EXAMPLE 1

One hundred parts of each of components (A) [carboxylic acid anhydrides] shown in Table 1 and each of components (B) [copper compounds] in an amount shown in Table 1 were uniformly mixed and pulverized in a mortar to prepare a deodorant composition. One gram of each of the deodorant compositions was subjected to an ammonia deodorizing test (concentration 50,000 ppm), a hydrogen sulfide deodorizing test (concentration 5,000 ppm) and a methyl mercaptan deodorizing test (concentration 5,000 ppm). The results are shown in Table 1.

TABLE 1

| Run No. | Deodorant component (A) 100 parts | Deodorant component (B) Type | Parts | Ratio of ammonia deodorization (%) 1 hour later | 5 hours later | 24 hours later | Ratio of methyl mercaptan deodorization (%) 1 hour later | 5 hours later | 24 hours later | Ratio of hydrogen sulfide deodorization (%) 24 hours later |
|---|---|---|---|---|---|---|---|---|---|---|
| This invention | | | | | | | | | | |
| 1-1 | Succinic anhydride | Copper sulfate pentahydrate | 0.2 | 32 | 65 | 100 | 10 | 23 | 55 | 100 |
| 1-2 | Succinic anhydride | Copper sulfate pentahydrate | 1 | 38 | 68 | 100 | 12 | 34 | 81 | 100 |
| 1-3 | Succinic anhydride | Copper sulfate pentahydrate | 5 | 40 | 70 | 100 | 23 | 49 | 100 | 100 |
| 1-4 | Succinic anhydride | Cupric chloride | 1 | 37 | 61 | 100 | 11 | 28 | 90 | 100 |
| 1-5 | Succinic anhydride | Copper chlorophyll | 5 | 29 | 64 | 100 | 15 | 38 | 88 | 100 |
| 1-6 | Methylsuccinic anhydride | Copper sulfate pentahydrate | 1 | 18 | 58 | 100 | 18 | 31 | 79 | 100 |
| 1-7 | Butyric anhydride | Copper sulfate pentahydrate | 1 | 22 | 61 | 100 | 21 | 35 | 82 | 100 |
| 1-8 | Propionic anhydride | Copper sulfate pentahydrate | 1 | 30 | 58 | 100 | 15 | 41 | 95 | 100 |
| 1-9 | Lauric anhydride | Copper sulfate pentahydrate | 1 | 37 | 62 | 100 | 18 | 45 | 98 | 100 |
| 1-10 | Polyacrylic anhydride*[1] | Copper sulfate pentahydrate | 1 | 35 | 78 | 100 | 22 | 44 | 99 | 100 |
| 1-11 | Phthalic anhydride | Copper naphthenate | 1 | 32 | 68 | 100 | 18 | 33 | 98 | 100 |
| 1-12 | Phthalic anhydride | Copper oleate | 1 | 30 | 65 | 100 | 15 | 38 | 99 | 100 |
| 1-13 | Phthalic anhydride | Copper oleate | 5 | 32 | 68 | 100 | 25 | 51 | 100 | 100 |
| 1-14 | Trimellitic anhydride | Copper oleate | 1 | 31 | 61 | 100 | 14 | 36 | 95 | 100 |
| 1-15 | Pyromellitic anhydride | Copper oleate | 1 | 35 | 65 | 100 | 15 | 38 | 96 | 100 |
| Comparative Example | | | | | | | | | | |
| 1-16 | — | — | — | 0 | 0 | 1 | 0 | 0 | 0 | 0 |
| 1-17 | Citric acid | — | — | 27 | 72 | 100 | 1 | 2 | 2 | 5 |
| 1-18 | Citric acid | Copper oleate | 1 | 23 | 69 | 100 | 5 | 13 | 42 | 22 |
| 1-19 | Ferrous sulfate/L-ascorbic*[2] acid | — | — | 38 | 68 | 100 | 1 | 2 | 5 | 100 |

*[1] Molecular weight of about 6,000; about 40% of carboxyl groups are changed to acid anhydride groups.
*[2] A mixture of ferrous sulfate ($FeSO_4 \cdot 7H_2O$) and L-ascorbic acid in a molar ratio of 1:0.05

From the results of Table 1, it becomes apparent that the deodorant compositions in this invention have excellent deodorizing activity against malodors of not only basic substances but also sulfur substances.

Referential Example 1

Each of alpha-olefins shown in Table 2 and an equimolar amount of maleic anhydride were autoclaved and subjected to addition reaction at 200° C. for 15 hours in the presence of a polymerization inhibitor. Subsequently, the unreacted alpha-olefin was removed under reduced pressure. There resulted ene reaction products I-V [components (A) of the deodorant compositions] of alpha,beta-unsaturated dicarboxylic acid anhydrides with various alpha-olefins shown in Table 2.

TABLE 2

| Addition reaction product | I | II | III | IV | V |
|---|---|---|---|---|---|
| Type of alpha-olefin and its carbon number | A*[1] 6-10 | B*[2] 16-18 | C*[3] 30-40 | D*[4] 12-14 | E*[5] 20-28 |
| Properties of the addition | | | | | |

TABLE 2-continued

| Addition reaction product | I | II | III | IV | V |
|---|---|---|---|---|---|
| reaction product | | | | | |
| Melting point (°C.) | −37 | 43 | 50 | 26 | 52 |
| Saponification value (KOH mg/g) | 537 | 312 | 192 | 361 | 222 |

*[1]DAILEN 610, a product of Mitsubishi Chemical Industries, Ltd.
*[2]DAILEN 168, a product of Mitsubishi Chemical Industries, Ltd.
*[3]DAILEN 30, a product of Mitsubishi Chemical Industries, Ltd.
*[4]DAILEN 124, a product of Mitsubishi Chemical Industries, Ltd.
*[5]DAILEN 208, a product of Mitsubishi Chemical Industries, Ltd.

EXAMPLE 2

Predetermined amounts of components (A) and (B) shown in Table 3 were taken, and a solvent shown in Table 3 was added thereto such that the whole system became 20 g to obtain a a solution of a deodorant composition. One gram of the solution was put in a 100-milliliter Erlenmeyer flask, and 1 ml of a nitrogen gas containing 20 mg of methyl mercaptan or 70 mg of ammonia per liter of $N_2$ was added thereto, and the flask was stopped. After the mixture was left to stand for 1 hour, the amount of methyl mercaptan or ammonia in the gaseous phase was measured by gas chromatography, and the deodorizing activity on methyl mercaptan or ammonia was evaluated. The results are shown in Table 3.

EXAMPLE 3

Each of the various solutions of deodorant compositions prepared in Example 2 was put in an ampoule and the ampoule was stopped. After left to stand for 1 week, the solution of the deodorant composition containing ferrous sulfate/L-ascorbic acid/copper sulfate pentahydrate became brown, and the ratio of methyl mercaptan deodorization was decreased to 35%. However, approximately the same results as in Example 2 were obtained on the other deodorant compositions.

These results reveal that the deodorant compositions in this invention are also excellent in storage stability.

EXAMPLE 4

One hundred parts of each of components (A) [alpha,beta-unsaturated dicarboxylic acid anhydride polymers] shown in Table 4 and each of components (B) [copper compounds] in an amount shown in Table 4 were uniformly mixed and pulverized to prepare a powdery sample. The samples were tested for thermal stability and deodorizing activity.

In the test of thermal stability, 1 g of each of the samples was left to stand at 150° C. for 1 hour in a hot air circulating oven and at that time a percentage loss of weight by heating (a) was measured. Each of these samples was further heated at 200° C. for 1 hour and at that time a percentage loss of weight by heating (b) was measured.

TABLE 3

| | Deodorant composition | | | | Ratio of methyl mercaptan deodorization (%) | Ratio of ammonia deodorization (%) |
|---|---|---|---|---|---|---|
| | (A) component | | (B) component | | | |
| Run No. | Type | Amount (mg) | Type | Amount (mg) | Solvent | | |

| Run No. | Type | Amount (mg) | Type | Amount (mg) | Solvent | Ratio of methyl mercaptan deodorization (%) | Ratio of ammonia deodorization (%) |
|---|---|---|---|---|---|---|---|
| This invention | | | | | | | |
| 3-1 | Phthalic anhydride | 1000 | Copper naphthenate | 50 | Toluene | 85 | 100 |
| 3-2 | Trimellitic anhydride | 1000 | Copper oleate | 50 | Toluene | 88 | 100 |
| 3-3 | Addition reaction product (II) in Referential Example 1 | 1000 | Copper oleate | 50 | Toluene | 90 | 100 |
| 3-4 | Addition reaction product (II) in Referential Example 1 | 1000 | Copper naphthenate | 50 | Dioctyl phthalate | 86 | 100 |
| Comparative Example | | | | | | | |
| 3-5 | Ferrous sulfate/*[1] L-ascorbic acid | 1000 | Copper sulfate pentahydrate | 50 | Water | 80 | 100 |
| 3-6 | Citric acid | 1000 | Copper sulfate pentahydrate | 50 | Water | 30 | 100 |

*[1]A mixture of ferrous sulfate ($FeSO_4 \cdot 7H_2O$) and L-ascorbic acid in a molar ratio of 1:0.05

From the above results of Table 3, it becomes apparent that the deodorant compositions in this invention have excellent deodorizing activity on methyl mercaptan and ammonia even in solution state.

In the deodorizing test, the aforesaid method was followed except that the amount of the sample was changed to 100 mg, the concentration of ammonia to 5,000 ppm and the concentration of methyl mercaptan to 500 ppm respectively.

The results are shown in Table 4.

TABLE 4

| Run No. | (A) component | (B) component Type | Parts | Percentage loss of weight by heating (%) (a) | (b) | Ratio of methyl mercaptan deodorization (%) | Ratio of ammonia deodorization (%) |
|---|---|---|---|---|---|---|---|
| This invention | | | | | | | |
| 4-1 | Styrene/maleic anhydride*[1] anhydride copolymer | Copper oleate | 1 | 9.0 | 10.1 | 80 | 100 |
| 4-2 | Styrene/maleic anhydride*[1] anhydride copolymer | Copper oleate | 2 | 9.1 | 11.1 | 100 | 100 |

TABLE 4-continued

| Run No. | (A) component | (B) component Type | Parts | Percentage loss of weight by heating (%) (a) | (b) | Ratio of methyl mercaptan deodorization (%) | Ratio of ammonia deodorization (%) |
|---|---|---|---|---|---|---|---|
| 4-3 | Styrene/maleic anhydride*¹ anhydride copolymer | Cupric chloride | 1 | 8.3 | 9.2 | 100 | 100 |
| 4-4 | Styrene/maleic anhydride*¹ anhydride copolymer | Copper chlorophyll | 1 | 9.1 | 10.4 | 50 | 100 |
| 4-5 | Isobutene/maleic*² anhydride copolymer | Copper oleate | 1 | 2.0 | 3.3 | 77 | 100 |
| 4-6 | Styrene/maleic anhydride*³ monoester copolymer | Copper oleate | 1 | 5.0 | 14.0 | 73 | 100 |
| Comparative Example | | | | | | | |
| 4-7 | Styrene/maleic anhydride copolymer | — | — | 8.4 | 9.7 | 5 | 100 |
| 4-8 | Ferrous sulfate/*⁴ L-ascorbic acid | — | — | 34.9 | 40.1 | 3 | 100 |
| 4-9 | Citric acid | — | — | 18.2 | 94.6 | 2 | 100 |

*¹SMA1000A, a product of Arco Chemical Company, copolymer composition ratio 50/50
*²ISOBAM-10, a product of Kurarey Isoprene Chemical Co., Ltd., copolymer composition ratio 50/50
*³SMA17352A, a product of Arco Chemical Company, copolymer composition ratio 50/50
*⁴Mixed in particulate state in a mixing ratio of 100:10

The results of Table 4 reveal that the deodorant compositions of this invention containing as component (A) the alpha,beta-unsaturated dicarboxylic acid anhydride polymers are excellent in thermal stability and deodorizing activity on basic substances and sulfur substances.

EXAMPLE 5

One hundred parts of each of components (A) [Diels-Alder addition reaction products of alpha,beta-unsaturated dicarboxylic acid anhydrides with olefins] and each of components (B) [copper compounds] in an amount shown in Table 5 were uniformly mixed and pulverized in a mortar to prepare a deodorant composition.

One gram of each of the deodorant compositions was subjected to an ammonia deodorizing test (concentration 50,000 ppm), a hydrogen sulfide deodorizing test or a methyl mercaptan deodorizing test (concentration 5,000 ppm). The results are shown in Table 5.

TABLE 5

| Run No. | (A) component | (B) component Type | Parts | Ratio of ammonia deodorization (%) 1 hour later | 5 hours later | 24 hours later | Ratio of hydrogen sulfide deodorization (%) 24 hours later | Ratio of methyl mercaptan deodorization (%) 1 hour later | 5 hours later | 24 hours later |
|---|---|---|---|---|---|---|---|---|---|---|
| This invention | | | | | | | | | | |
| 5-1 | Addition reaction product (I) in Referential Example 1 | Copper oleate | 1 | 37 | 82 | 100 | 100 | 12 | 30 | 80 |
| 5-2 | Addition reaction product (II) in Referential Example 1 | Copper oleate | 1 | 21 | 57 | 100 | 100 | 12 | 28 | 77 |
| 5-3 | Addition reaction product (III) in Referential Example 1 | Copper oleate | 1 | 13 | 29 | 68 | 100 | 11 | 27 | 73 |
| 5-4 | Addition reaction product (I) in Referential Example 1 | Copper oleate | 0.2 | 39 | 84 | 100 | 100 | 10 | 24 | 65 |
| 5-5 | Addition reaction product (I) in Referential Example 1 | Copper oleate | 5 | 33 | 73 | 100 | 100 | 44 | 98 | 100 |
| 5-6 | Addition reaction product (I) in Referential Example 1 | Cupric chloride | 1 | 37 | 82 | 100 | 100 | 22 | 49 | 100 |
| 5-7 | Addition reaction product (I) in Referential Example 1 | Copper chlorophyll | 1 | 37 | 82 | 100 | 100 | 8 | 19 | 50 |
| 5-8 | 3-Methyl-Δ⁴-tetrahydrophthalic anhydride | Copper oleate | 1 | 21 | 47 | 95 | 100 | 11 | 27 | 72 |
| Comparative Example | | | | | | | | | | |
| 5-9 | Addition reaction product (I) in Referential Example 1 | — | — | 38 | 85 | 100 | 100 | 1 | 2 | 5 |
| 5-10 | Ferrous sulfate/L-ascorbic*¹ acid | — | — | 38 | 68 | 100 | 100 | 1 | 1 | 3 |
| 5-11 | Citric acid | — | — | 27 | 72 | 100 | 5 | 1 | 2 | 2 |
| 5-12 | Citric acid | Copper oleate | 1 | 23 | 69 | 100 | 22 | 5 | 13 | 42 |
| 5-13 | (none) | Copper oleate | — | 0 | 1 | 3 | 100 | 90 | 100 | — |

*¹A mixture of ferrous sulfate (FeSO₄ 7H₂O) and L-ascorbic acid in a molar ratio of 1:0.05

The results of Table 5 reveal that the deodorant compositions in this invention using as component (A) the Diels-Alder addition reaction products of alpha,beta-unsaturated dicarboxylic acid anhydrides with olefins show excellent deodorizing activity on not only basic substances but also sulfur substances.

REFERENTIAL EXAMPLE 2 stretched. There were obtained films (1) to (20) each having a thickness of 0.1 mm.

TABLE 6

| Film | Deodorant composition | | | | Thermoplastic resin Type |
|---|---|---|---|---|---|
| | Amount*1 (parts) | (A) component Type | (B) component Type | Amount*2 (parts) | |
| (1) | 2.5 | Phthalic anhydride | Copper naphthenate | 1 | Low-density*3 polyethylene |
| (2) | 2.5 | Phthalic anhydride | Copper oleate | 1 | Low-density*3 polyethylene |
| (3) | 2.5 | Phthalic anhydride | Copper oleate | 5 | Low-density*3 polyethylene |
| (4) | 0.0 | Phthalic anhydride | Copper oleate | 1 | Low-density*3 polyethylene |
| (5) | 2.5 | Trimellitic anhydride | copper oleate | 1 | Low-density*3 polyethylene |
| (6) | 2.5 | Pyromellitic anhydride | Copper oleate | 1 | Low-density*3 polyethylene |
| (7) | 2.5 | Succinic anhydride | Copper naphthenate | 1 | Low-density*3 polyethylene |
| (8) | 2.5 | Succinic anhydride | Copper oleate | 1 | Low-density*3 polyethylene |
| (9) | 2.5 | Succinic anhydride | Copper oleate | 5 | Low-density*3 polyethylene |
| (10) | 10.0 | Succinic anhydride | Copper oleate | 1 | Low-density*3 polyethylene |
| (11) | 2.5 | Lauric anhydride | Copper naphthenate | 1 | Low-density*3 polyethylene |
| (12) | 2.5 | Lauric anhydride | Copper oleate | 1 | Low-density*3 polyethylene |
| (13) | 2.5 | 1,2-cyclohexanedi-carboxylic anhydride | Copper naphthenate | 1 | Low-density*3 polyethylene |
| (14) | 2.5 | 1,2-cyclohexanedi-carboxylic anhydride | Copper oleate | 1 | Low-density*3 polyethylene |
| (15) | 2.5 | Phthalic anhydride | Copper naphthenate | 1 | Polypropylene*4 |
| (16) | 10.0 | Phthalic anhydride | Copper naphthenate | 1 | Polypropylene*4 |
| (17) | 2.5 | Pyromellitic anhydride | Copper naphthenate | 1 | Polypropylene*4 |
| (18) | 2.5 | Citric acid | — | — | Low-density*3 polyethylene |
| (19) | 2.5 | Phthalic acid | — | — | Low-density*3 polyethylene |
| (20) | 2.5 | Lauric acid | — | — | Low-density*3 polyethylene |

*1Amount of a deodorant composition per 100 parts of a thermoplastic resin
*2Amount per 100 parts of (A) component
*3SHOLEX 720FS, a product of Showa Denko K. K.
*4SHO-ALLOMER MX-201, a product of Showa Denko K. K.

One hundred parts of each of the thermoplastic resins shown in Table 6 and each of the deodorant compositions shown in Table 6 were mixed by a Henschel mixer to obtain a deodorant resin composition. The resulting deodorant resin composition was extrusion molded into a film. That is, a sheet was extruded through a T-die using an extruder having an inner diameter of 65 mm and a screw compression ratio of 5.0, and biaxially

EXAMPLE 6

Each of the films (1) to (20) shown in Table 6 was subjected to an ammonia, hydrogen sulfide or methyl mercaptan deodorizing test. The results are shown in Table 7. In these tests, the concentration of ammonia was 20,000 ppm and the concentration of methyl mercaptan was 300 ppm.

TABLE 7

| | Film | Ratio of ammonia deodorization (%) | | | Ratio of hydrogen sulfide deodorization (%) | | | Ratio of methyl mercaptan deodorization (%) | | |
|---|---|---|---|---|---|---|---|---|---|---|
| | | 1 hour later | 5 hours later | 24 hours later | 1 hour later | 5 hours later | 24 hours later | 1 hour later | 5 hours later | 24 hours later |
| This invention | (1) | 11 | 33 | 75 | 18 | 47 | 100 | 17 | 58 | 100 |
| | (2) | 15 | 38 | 86 | 15 | 45 | 100 | 14 | 59 | 100 |
| | (3) | 18 | 42 | 90 | 20 | 56 | 100 | 41 | 88 | 100 |
| | (4) | 42 | 87 | 100 | 30 | 78 | 100 | 20 | 70 | 100 |
| | (5) | 12 | 37 | 76 | 14 | 41 | 100 | 18 | 49 | 98 |
| | (6) | 15 | 40 | 81 | 11 | 50 | 100 | 14 | 55 | 100 |
| | (7) | 13 | 35 | 78 | 18 | 48 | 100 | 19 | 58 | 100 |
| | (8) | 13 | 32 | 76 | 21 | 48 | 100 | 16 | 58 | 100 |
| | (9) | 15 | 31 | 80 | 21 | 56 | 100 | 38 | 88 | 100 |
| | (10) | 48 | 88 | 100 | 28 | 76 | 100 | 14 | 48 | 98 |
| | (11) | 18 | 28 | 74 | 11 | 42 | 97 | 11 | 47 | 97 |
| | (12) | 12 | 25 | 68 | 10 | 38 | 95 | 12 | 42 | 96 |
| | (13) | 15 | 32 | 74 | 18 | 30 | 98 | 15 | 47 | 99 |
| | (14) | 17 | 39 | 81 | 17 | 41 | 100 | 19 | 41 | 100 |
| | (15) | 13 | 40 | 82 | 13 | 38 | 100 | 15 | 50 | 100 |
| | (16) | 48 | 87 | 100 | 30 | 84 | 100 | 14 | 55 | 100 |

TABLE 7-continued

| | | Ratio of ammonia deodorization (%) | | | Ratio of hydrogen sulfide deodorization (%) | | | Ratio of methyl mercaptan deodorization (%) | | |
|---|---|---|---|---|---|---|---|---|---|---|
| Film | | 1 hour later | 5 hours later | 24 hours later | 1 hour later | 5 hours later | 24 hours later | 1 hour later | 5 hours later | 24 hours later |
| | (17) | 15 | 42 | 78 | 11 | 41 | 100 | 18 | 42 | 100 |
| Comparative | (18) | 10 | 21 | 54 | 5 | 9 | 12 | 2 | 3 | 5 |
| Example | (19) | 11 | 29 | 68 | 5 | 10 | 15 | 2 | 5 | 8 |
| | (20) | 5 | 18 | 41 | 2 | 6 | 8 | 1 | 3 | 6 |

The results of Table 7 reveal that the films shaped from the deodorant resin compositions of this invention have excellent deodorizing activity on basic substances and sulfur substances.

REFERENTIAL EXAMPLE 3

Referential Example 2 was repeated except using 100 parts of each of thermoplastic resins shown in Table 8 and each of deodorant compositions shown in Table 8. There resulted films (21) to (27). The resulting films were odorless.

The results of Tables 8 and 9 reveal that the films obtained from the deodorant resin compositions of this invention containing the alpha,beta-unsaturated dicarboxylic acid anhydride polymers as component (A) are more useful as a deodorant having a deodorizing activity on basic substances and sulfur substances than the films obtained from the conventional deodorant resin compositions. This is because the alpha,beta-unsaturated dicarboxylic acid anhydride polymer is considered better in thermal stability and compatibility with the thermoplastic resin.

TABLE 8

| | Deodorant composition | | | | | |
|---|---|---|---|---|---|---|
| | (A) component | | (B) component | | Thermoplastic resin | |
| Film | Type | Amount (parts) | Type | Amount (parts) | Type | Condition of film |
| (21) | Styrene/maleic anhydride*1 copolymer | 2.46 | Copper oleate | 0.1 | Low-density*3 polyethylene | Yellowish green, transparent |
| (22) | Styrene/maleic anhydride*1 copolymer | 2.46 | " | 0.2 | Low-density*3 polyethylene | Yellowish green, transparent |
| (23) | Styrene/maleic anhydride*1 copolymer | 2.46 | Cupric chloride | 0.1 | Low-density*3 polyethylene | Pale brown, transparent |
| (24) | Styrene/maleic anhydride*2 monoester copolymer | 2.46 | Copper oleate | 0.1 | Low-density*3 polyethylene | Yellowish green, transparent |
| (25) | Styrene/maleic anhydride*1 copolymer | 2.46 | " | 0.1 | Polypropylene*4 | Yellowish green, transparent |
| (26) | Citric acid | 2.46 | " | 0.2 | Low-density*3 polyethylene | Yellow, transparent with bubbles |
| (27) | Styrene/maleic anhydride*1 copolymer | 2.46 | " | 0.1 | Polypropylene*4 | Colorless, transparent |

*1SMA1000A, a product of Arco Chemical Company, copolymer composition ratio 50/50
*2SMA17352A, a product of Arco Chemical Company, copolymer composition ratio 50/50
*3SHOLEX 720FS, a product of Showa Denko K. K.
*4Polypro S205, a product of Tonen Sekiyu Kagaku K. K.

EXAMPLE 7

The films obtained in Referential Example 3 were subjected to a deodorizing test. In this test, the concentration of ammonia was 25,000 ppm and the concentration of methyl mercaptan was 300 ppm. The results are shown in Table 9.

REFERENTIAL EXAMPLE 4

Referential Example 2 was repeated except using 100 parts of each of thermoplastic resins shown in Table 10 and each of deodorant compositions shown in Table 10. There were obtained films (31) to (39).

TABLE 9

| | | Ratio of ammonia deodorization (%) | | | Ratio of methyl mercaptan deodorization (%) | | |
|---|---|---|---|---|---|---|---|
| Film | | 1 hour later | 4.5 hours later | 24 hours later | 2 hours later | 20 hours later | 68 hours later |
| This | (21) | 12.3 | 24.4 | 54.3 | 17.5 | 56.3 | 100 |
| invention | (22) | 12.5 | 25.4 | 56.7 | 30.6 | 81.5 | 100 |
| | (23) | 10.2 | 20.5 | 50.8 | 37.2 | 86.1 | 100 |
| | (24) | 12.5 | 23.8 | 48.5 | 17.8 | 59.0 | 100 |
| | (25) | 10.4 | 17.4 | 49.4 | 17.0 | 54.4 | 100 |
| Comparative | (26) | 5.8 | 9.9 | 19.1 | 0.0 | 0.3 | 0.5 |
| Example | (27) | 14.6 | 28.9 | 64.4 | 1.1 | 3.5 | 6.3 |

TABLE 10

| Film | Deodorant composition | | | | Thermoplastic resin Type |
|---|---|---|---|---|---|
| | Amount[*1] (parts) | (A) component Type | (B) component Type | Amount[*2] (parts) | |
| (31) | 2.5 | Addition reaction product (III) in Referential Example 1 | Copper oleate | 1 | Low-density[*3] polyethylene |
| (32) | 2.5 | Addition reaction product (III) in Referential Example 1 | " | 5 | Low-density[*3] polyethylene |
| (33) | 2.5 | Addition reaction product (III) in Referential Example 1 | Cupric chloride | 1 | Low-density[*3] polyethylene |
| (34) | 10.0 | Addition reaction product (III) in Referential Example 1 | Copper oleate | 1 | Low-density[*3] polyethylene |
| (35) | 2.5 | Addition reaction product (II) in Referential Example 1 | " | 1 | Low-density[*3] polyethylene |
| (36) | 2.5 | 3-Methyl-$\Delta^4$-tetrahydrophthalic anhydride | " | 1 | Low-density[*3] polyethylene |
| (37) | 2.5 | Addition reaction product (III) in Referential Example 1 | " | 1 | Polypropylene[*4] |
| (38) | 2.5 | Addition reaction product (III) in Referential Example 1 | — | — | Low-density[*3] polyethylene |
| (39) | 2.5 | Citric acid | — | — | Low-density[*3] polyethylene |

[*1]Amount of a deodorant composition per 100 parts of a thermoplastic resin
[*2]Amount per 100 parts of (A) component
[*3]SHOLEX 720FS, a product of Showa Denko K. K.
[*4]SHO-ALLOMER MX-201, a product of Showa Denko K. K.

EXAMPLE 8

Each of the films (31) to (39) was subjected to an ammonia or methyl mercaptan deodorizing test in the same way as in Example 6. The results are shown in Table 11.

TABLE 11

| | | Ratio of ammonia deodorization (%) | | | Ratio of methyl mercaptan deodorization (%) | | |
|---|---|---|---|---|---|---|---|
| Film | | 1 hour later | 5 hours later | 24 hours later | 1 hour later | 5 hours later | 24 hours later |
| This invention | (31) | 13 | 32 | 60 | 18 | 56 | 100 |
| | (32) | 12 | 31 | 60 | 55 | 97 | 100 |
| | (33) | 10 | 28 | 57 | 37 | 86 | 100 |
| | (34) | 44 | 100 | — | 61 | 100 | — |
| | (35) | 25 | 61 | 100 | 18 | 59 | 100 |
| | (36) | 7 | 18 | 34 | 19 | 58 | 100 |
| | (37) | 12 | 30 | 56 | 17 | 54 | 100 |
| Comparative Example | (38) | 14 | 33 | 61 | 2 | 4 | 5 |
| | (39) | 7 | 12 | 20 | 0 | 0 | 0 |

The results of Table 11 show that the shaped articles produced from the deodorant resin compositions of this invention containing as component (A) Diels-Alder addition reaction products have excellent deodorizing activity on basic substances and sulfur substances.

REFERENTIAL EXAMPLE 5-1

To 100 parts of a polyvinyl chloride resin (NIPEON A-33, a product of Nippon Zeon Co., Ltd.) were added 3 parts of a barium-zinc-type heat stabilizer, 6 parts of an azodicarbonamide blowing agent, 15 parts of titanium oxide, 80 parts of calcium carbonate, 65 parts of dioctyl phthalate and 5 parts of mineral spirits. They were slurried by a mixing and grinding machine, and a powder of a styrene/maleic anhydride copolymer (SMA 1000A, a product of Arco Chemical Company, copolymer composition ratio 50/50) in an amount corresponding to 5% of the whole solids content of the slurry and copper naphthenate in an amount corresponding to 10% of the copolymer were further added to the slurry. The mixture was further mixed for 5 minutes to obtain a paste sol. Said paste sol was coated on a paper to a thickness of 200 microns by a bar coater, and the coated paper was then treated at 210° C. for 60 seconds in a hot air circulating oven to afford a foamed sheet (1b).

REFERENTIAL EXAMPLES 5-2 TO 5-15

Using expandable thermoplastic resins and deodorant compositions shown in Table 12, foamed sheets (2b) to (15b) were produced in the same way as in Referential Example 5-1.

TABLE 12

| Foamed sheet | Expandable thermoplastic resin | Deodorant compostion | | | |
|---|---|---|---|---|---|
| | | (A) component | | (B) component | |
| | | Type | Amount[*1] (%) | Type | Amount[*2] (%) |
| (2b) | Polyvinyl chloride resin[*3] | Styrene/maleic anhydride[*5] copolymer | 5 | Copper naphthenate | 20 |
| (3b) | " | 1-Octadecene/maleic[*6] anhydride copolymer | 5 | Cupric chloride | 10 |
| (4b) | Vinyl acetate/vinyl[*4] | Styrene/maleic anhydride[*5] | 5 | Copper naphthenate | 10 |

TABLE 12-continued

| Foamed sheet | Expandable thermoplastic resin | Deodorant compostion (A) component Type | Amount[*1] (%) | (B) component Type | Amount[*2] (%) |
|---|---|---|---|---|---|
| (5b) | chloride copolymer resin Polyvinyl chloride resin[*3] | copolymer Addition reaction product (IV) in Referential Example 1 | 5 | " | 10 |
| (6b) | " | Addition reaction product (II) in Referential Example 1 | 5 | " | 10 |
| (7b) | " | Addition reaction product (V) in Referential Example 1 | 5 | " | 10 |
| (8b) | " | Succinic anhydride | 5 | " | 10 |
| (9b) | " | 3-Methyl-$\Delta^4$-tetrahydro-phthalic anhydride | 5 | " | 10 |
| (10b) | " | Lauric anhydride | 5 | " | 10 |
| (11b) | " | Polyacrylic anhydride[*7] | 5 | " | 10 |
| (12b) | " | Phthalic anhydride | 5 | " | 10 |
| (13b) | " | Trimellitic anhydride | 5 | " | 10 |
| (14b) | " | Pyromellitic anhydride | 5 | " | 10 |
| (15b) | " | — | — | — | — |

[*1]% By weight based on the solids content of a slurry
[*2]% By weight based on (A) component
[*3]same as used in Referential Example 6-1
[*4]NIPEON A-135J, a product of Nippon Zeon Co., Ltd.
[*5]Same as used in Referential Example 6-1
[*6]PA-18, a product of Gulf Oil Chemicals Company, copolymer composition ratio 50/50
[*7]Molecular weight of about 6000; about 40% of carboxyl groups are changed to acid anhydride groups.

REFERENTIAL EXAMPLE 5-16

A 1-octadecene/maleic anhydride copolymer (PA-18, a product of Gulf Oil Chemicals Company, copolymer composition ratio 50/50) and copper naphthenate in an amount corresponding to 10% of said copolymer were dissolved in toluene to prepare a 5% toluene solution. Said solution was impregnated in the foamed sheet (15b) obtained in Referential Example 5-15 and dried to give a foamed sheet (16b) wherein the amount of the deodorant composition adhered was 5%.

EXAMPLE 9

The foamed sheets (1b) to (16b) obtained in Referential Examples 5-1 to 5-16 were subjected to an ammonia or methyl mercaptan deodorizing test. In this Example, the amount of the sample (foamed sheet) was 0.5 g, and the inside of the ampoule was replaced with a nitrogen gas containing 3,800 ppm of ammonia or 100 ppm of methyl mercaptan. The results are shown in Table 13.

TABLE 13

| Foamed sheet | | Ratio of ammonia deodorization (%) 5 hours later | 24 hours later | Ratio of methyl mercaptan deodorization (%) 5 hours later | 24 hours later |
|---|---|---|---|---|---|
| This invention | 1(b) | 34 | 100 | 69 | 100 |
| | 2(b) | 32 | 100 | 100 | — |
| | 3(b) | 26 | 81 | 62 | 98 |
| | 4(b) | 38 | 100 | 72 | 100 |
| | 5(b) | 43 | 100 | 58 | 99 |
| | 6(b) | 35 | 92 | 61 | 100 |
| | 7(b) | 35 | 95 | 66 | 100 |
| | 8(b) | 51 | 100 | 70 | 100 |
| | 9(b) | 54 | 100 | 72 | 100 |
| | 10(b) | 38 | 85 | 65 | 95 |
| | 11(b) | 37 | 98 | 62 | 98 |
| | 12(b) | 38 | 100 | 68 | 99 |
| | 13(b) | 38 | 100 | 62 | 98 |
| | 14(b) | 34 | 100 | 68 | 100 |
| | 16(b) | 46 | 100 | 78 | 100 |
| Comparative Example | 15(b) | 24 | 28 | 1 | 2 |

The above results of Table 13 reveal that the deodorant foams produced from the deodorant compositions of this invention have excellent deodorizing activity on ammonia and methyl mercaptan.

EXAMPLE 10

One gram of each of the paste sols prepared in Referential Examples 5-1 and 5-15 was put in a 150-milliliter ampoule, and the ampoule was stopped. Said ampoule was dipped in an oil bath of 220° C. for 10 minutes to expand the paste sol. Thereafter, the ampoule was opened and the odor in the gaseous phase was examined. A strong ammonia odor was given off from the gaseous phase of Referential Example 5-15, but the gaseous phase of Referential Example 5-1 was odorless. Moreover, the odor of the foam in the ampoule was examined. As a result, the foam of Referential Example 5-1 had no ammonia odor, while the foam of Referential Example 5-15 had ammonia odor.

The above results show that when the deodorant foam is prepared by expanding the expandable thermoplastic resin containing the deodorant composition of this invention, it is extremely preventable to diffuse the ammonia odor occurring due to decomposition of the blowing agent.

EXAMPLE 11

Foamed sheets (1a), (2a), (3a) and (15a) were produced in the same way as in Referential Examples 5-1, 5-2, 5-3 and 5-15 except that the heat treating time was changed to 30 seconds. Likewise, foamed sheets (1c), (2c), (3c) and (15c) were produced except that the heat treating time was changed to 90 seconds. The expansion ratios of these foamed sheets and the foamed sheets (1b), (2b), (3b) and (15b) were measured with the results shown in Table 14.

TABLE 14

| Foamed sheet | | Expansion ratio a | b | c |
|---|---|---|---|---|
| This invention | 1 | 1.49 | 6.55 | 8.07 |
| | 2 | 1.48 | 6.58 | 8.02 |
| | 3 | 1.50 | 6.47 | 8.15 |

TABLE 14-continued

| Foamed sheet | Expansion ratio | | |
| --- | --- | --- | --- |
| | a | b | c |
| Comparative Example 15 | 1.45 | 6.44 | 8.20 |

The above results of Table 14 reveal that the deodorant compositions of this invention do not affect the shapes of the foams.

What we claim is:

1. A deodorant composition comprising (A) a compound having an acid anhydride group in the molecule selected from the group consisting of (1) a polymer having units derived from an alpha, beta-unsaturated dicarboxylic acid anhydride, (2) a Diels-Alder addition reaction product of an alpha, beta-unsaturated dicarboxylic acid anhydride with an olefin its derivative, and (3) an anhydride of an aliphatic, alicyclic or aromatic monocarboxylic or a polycarboxylic acid anhydride, and (4) an ene reaction product of an alpha, beta-unsaturated dicarboxylic acid anhydride with an olefin and its derivative, and (B) a copper salt of an inorganic acid or a copper salt of a monomeric organic acid; and when the compound (A) having an acid anhydride group in the molecule is the polymer (1) having units derived from an alpha, beta-unsaturated dicarboxylic acid anhydride, said polymer is a homopolymer of an alpha, beta-unsaturated dicarboxylic acid anhydride, a copolymer of an alpha, beta-unsaturated dicarboxylic acid anhydride with a monomer copolymerizable therewith selected from the group consisting of styrene, alpha-methyl-styrene, vinyltoluene, isobutene, 1-butene, 2-butene, 1-pentene, 2-pentene, 2-methyl-1-butene, 2-methyl-2-butene, 1-hexene, 2,2,4-trimethyl-1-pentene, 2,2,4-trimethyl-2-pentene, 1-decene, 1-octadecene, cyclopentene, cyclohexene, cyclooctene, butadiene, isoprene and piperylene, or said homopolymer or copolymer in which a portion of said acid anhydride groups are converted to carboxyl groups.

2. The deodorant composition of claim 1 wherein (A) the compound having the acid anhydride group in the molecule is a copolymer of maleic anhydride or a maleic anhydride monoester and a monoolefin selected from the group consisting of styrene, alpha-methyl-styrene, vinyltoluene, isobutene, 1-butene, 2-butene, 1-pentene, 2-pentene, 2-methyl-1-butene, 2-methyl-2-butene, 1-hexene, 2,2,4-trimethyl-1-pentene, 2,2,4-trimethyl-2-pentene, 1-decene, 1-octadecene, cyclopentene, cyclohexene, and cyclooctene.

3. The deodorant composition of claim 1 wherein (A) the compound having the acid anhydride group in the molecule is an ene reaction product of maleic anhydride with an alpha-olefin.

4. The deodorant composition of any one of claims 1, 2 or 3 wherein the weight ratio of (A) the compound having the acid anhydride group in the molecule to (B) the copper compound is 100:0.01 to 100:200.

5. The deodorant composition of any one of claims 1, 2 or 3 which is in the form of a powder.

6. The deodorant composition of any one of claims 1, 2 or 3 which is in the form of a solution.

7. The deodorant composition of claim 1, wherein the copper compound (B) is a copper salt of an inorganic acid selected from the group consisting of copper sulfate, copper nitrate, cuprous chloride, cupric chloride, cuprous bromide, curpic bromide, cuprous iodide and copper carbonate.

8. The composition of claim 1, wherein the copper compound (B) is a copper salt of an organic acid selected from the group consisting of copper acetate, cupric citrate, copper gluconate, copper malate, copper glyoxylate, copper 2-ketoglutarate, copper pyruvate, copper oxaloacetate, copper oleate and copper naphthenate.

9. The deodorant composition of claim 1, wherein the component (A) is the compound (1) which is said homopolymer of the alpha, beta-unsaturated carboxylic acid.

10. The deodorant composition of claim 1, wherein said component (A) is said polymer (1) which is the copolymer of the alpha, beta-unsaturated carboxylic acid anhydride with said copolymerizable comonomer.

11. The deodorant composition of claim 1, wherein the component (A) is the Diels-Alder addition reaction product of the alpha, beta-unsaturated dicarboxylic acid anhydride with an olefin.

12. The deodorant composition of claim 1, wherein the component (A) is the anhydride of an aliphatic, alicylic or aromatic monocarboxylic or polycarboxylic acid anhydride.

* * * * *

UNITED STATES PATENT AND TRADEMARK OFFICE
CERTIFICATE OF CORRECTION

PATENT NO. : 4,959,207
DATED : September 25, 1990
INVENTOR(S) : UEDA, ET AL.

It is certified that error appears in the above-identified patent and that said Letters Patent is hereby corrected as shown below:

COLUMN 21, LINE 18;

Claim 1, line 7, between "olefin" and "its", insert --and--, after "derivatives", delete "and".

Signed and Sealed this

Twenty-first Day of July, 1992

*Attest:*

DOUGLAS B. COMER

*Attesting Officer*      *Acting Commissioner of Patents and Trademarks*